(12) United States Patent
Kamiyama

(10) Patent No.: US 6,638,225 B2
(45) Date of Patent: Oct. 28, 2003

(54) ULTRASONIC DIAGNOSIS APPARATUS

(75) Inventor: Naohisa Kamiyama, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 09/953,923

(22) Filed: Sep. 18, 2001

(65) Prior Publication Data

US 2002/0035329 A1 Mar. 21, 2002

(30) Foreign Application Priority Data

Sep. 18, 2000 (JP) ...................................... 2000-282067

(51) Int. Cl.<sup>7</sup> ................................................ A61B 8/00
(52) U.S. Cl. ...................................................... 600/443
(58) Field of Search ................................ 600/443, 447, 600/449, 444, 455, 456; 128/916

(56) References Cited

U.S. PATENT DOCUMENTS

| 4,773,425 | A | | 9/1988 | Saitou |
| 5,860,927 | A | * | 1/1999 | Sakaguchi et al. ........... 600/453 |
| 6,149,597 | A | | 11/2000 | Kamiyama |
| 6,222,795 | B1 | | 4/2001 | Hossack et al. |
| 6,443,896 | B1 | * | 9/2002 | Detmer ........................ 600/445 |
| 6,447,453 | B1 | * | 9/2002 | Roundhill et al. ........... 600/443 |

* cited by examiner

Primary Examiner—Francis J. Jaworski
Assistant Examiner—Maulin Patel
(74) Attorney, Agent, or Firm—Oblon, Spivak, McClelland, Maier & Neustadt, P.C.

(57) ABSTRACT

An ultrasonic diagnosis apparatus scans inside of a subject with an ultrasonic wave to obtain a cross-sectional image. A reference image in which a portion as a reference for holding an equal cross-section is extracted from an image being diagnosed is generated. The reference image is displayed as a still image, superimposed on a motion image.

21 Claims, 6 Drawing Sheets

Numbers indicate drive voltage values (V) or relative values taking maximum value of drive voltage as 100

ULTRASONIC DIAGNOSIS APPARATUS

BACKGROUND OF THE INVENTION

1. Field of the Invention

The present invention relates to an ultrasonic diagnosis apparatus which efficiently executes a diagnosis/analysis protocol aiming measurement, in a contrast echo method mainly used for transient diagnosis.

2. Description of the Related Art

By ultrasonic diagnosis, pulsation of a heart and motion of an embryo can be obtained as real time display by a simple operation of contacting an ultrasonic probe from the body surface, and high safety can be ensured. Therefore, inspection can be repeatedly performed. In addition, the scale of the system is smaller compared with other diagnosis apparatuses using X-rays, CT, MRI, and the like, so it is convenient that inspection can also be easily performed after moving to the bed side. It is also advantageous that there are no influences of exposure unlike the case of using X-rays.

A photography method based on this ultrasonic diagnosis apparatus is a contrast echo method using an ultrasonic contrast agent of vein application type. For example, in this contrast method, an ultrasonic contrast agent is injected through a vein to strengthen a blood signal in inspection on a heart, a ventral organ, or the like, for the purpose of evaluating blood kinetics. In many contrast agents, micro bubbles serve as a reflection source, and the contrast effect increases as the injection amount and concentration increase. Meanwhile, it has been found that bubbles are broken by ultrasonic irradiation due to the characteristic of the base material of bubbles, so that the contrast effect time is shortened or so.

In recent years, many developments have been made in the quantitative analysis method for evaluating blood kinetics. The most basic method is the measurement of a so-called time intensity curve (TIC) in which the process of strengthening an echo signal in an interested area after application of a contrast agent is traced and time-based change of the luminance thereof is expressed in form of a graph.

In general, in quantitative analysis, even if the method is logically proper, deterioration of the precision in analysis can be easily expected unless measurement data which matches with the analysis is obtained. Factors which deteriorate the analysis precision exist in many aspects, e.g., the doctor who scans a patient with use of the system, the inspection engineer (hereinafter the person who uses an ultrasonic diagnosis apparatus is simply called an "operator"), organic functions of a patient, and the like.

For example, the factors existing in the body of the diagnosis system are considered to be the cases that the essential S/N ratio of the system is too low to obtain a signal sufficient for analysis, the output signal of the system becomes non-uniform in the plane of a diagnosis fault under influences of organic attenuation or the like so that the analysis values differ between respective parts.

Factors existing in the operator are considered to be a case that a cross-section shifts gradually without intentions even if it is necessary to record continuously image information of one same cross-section, and the like.

Factors existing in the organic functions are considered to be deterioration of analysis precision, based on breath or fluctuation of heartbeat. For example, change of the blood speed due to pulsation is an undesired phenomenon if the analysis assumption is a constant flow.

The present invention has been made in view of the above situation and has an object of providing a support function to reduce the error factor of analysis as much as possible or when a diagnosis protocol mainly aiming measurement is executed, or an analysis method using the function.

BRIEF SUMMARY OF THE INVENTION

According to a first aspect of the present invention, there is provided an ultrasonic diagnosis apparatus for scanning inside of a subject with an ultrasonic wave to obtain a cross-sectional image comprises: an image generator configured to generate a reference image in which a portion as a reference for holding an equal cross-section is extracted from an image being diagnosed; and a display device configured to display the reference image as a still image, superimposed on a motion image.

According to a second aspect of the present invention, there is provided an ultrasonic diagnosis apparatus for scanning inside of a subject applied with a contrast agent, with an ultrasonic wave, to obtain a cross-sectional image, comprises: a display device configured to display an ultrasonic image; a specification device configured to allow an operator to specify an area of the ultrasonic diagnosis image displayed; and a transmitting unit configured to transmit an ultrasonic wave such that a focus point of transmitting ultrasonic wave is varied to exist in the area specified by the specification device.

According to a third aspect of the present invention, there is provided an ultrasonic diagnosis apparatus comprises: a memory configured to store a plurality of diagnosis image groups in each of which a plurality of diagnosis images collected at a pre-determined cycle based on an organic signal of a subject are arranged based on time; and a display device configured to display simultaneously the plurality of diagnosis image groups such that time phases in the predetermined cycle correspond between the groups.

According to a forth aspect of the present invention, there is provided an ultrasonic diagnosis apparatus comprises: an ultrasonic probe configured to transmit an ultrasonic wave to a subject and receive the ultrasonic wave from the subject; a receiving unit configured to obtain electrocardiogram signal; a generator configured to generate an ultrasonic image based on the signal received by the ultrasonic probe; and an analyzer configured to analyze a luminance change curve based on the ultrasonic image obtained when the electrocardiogram signal is at one same heartbeat phase.

According to a fifth aspect of the present invention, there is provided an ultrasonic diagnosis apparatus comprises: an ultrasonic probe configured to transmit an ultrasonic wave to a subject and receive the ultrasonic wave from the subject; a generator configured to generate ultrasonic images based on the signal received by the ultrasonic probe; a memory configured to store a reference image which is an ultrasonic image to adjust a scan position; and a display device configured to display the ultrasonic images generated by the generator as a real-time motion image, superimposed the reference image.

According to the configuration described above, it is possible to realize an ultrasonic diagnosis apparatus comprising a support function to reduce factors causing analysis errors as much as possible when a diagnosis protocol aiming measurement is executed, and an analysis method using the function.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

In the following, first to third embodiments of the present invention will be explained in accordance with the drawings. Note that the ultrasonic diagnosis apparatus according to the present invention has support functions and the like which can be used in the case where a diagnosis protocol aiming measurement is executed or the case where a diagnosis protocol is executed in measurement of the blood speed and the blood amount in veins and heart such as quantitative analysis using a contrast agent (TIC). The following explanation will be made with respect to an example of the case where a diagnosis protocol concerning quantitative analysis (ITC) using a contrast agent is used, for convenience of explanation. Also, in the following explanation, those components that have substantially the same functions and structures will be denoted at the same reference symbols, and reiterative explanation thereof will be made if it is necessary.

First Embodiment

Figure 1:
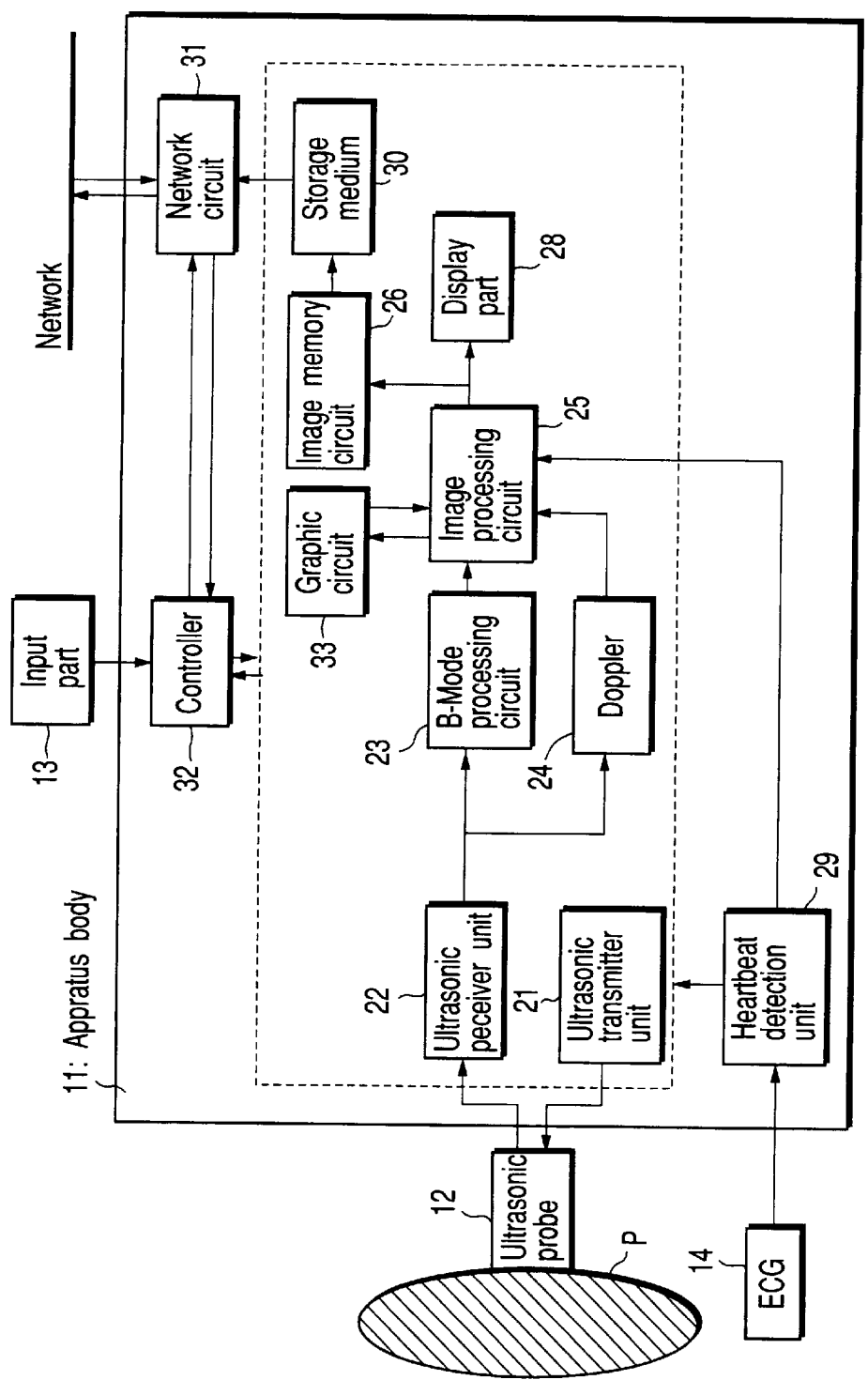
FIG. 1 is a block diagram showing the schematic structure of an ultrasonic diagnosis apparatus 10 according to the first and second embodiments of the present invention.

FIG. 1 is a block diagram showing the schematic structure of an ultrasonic diagnosis apparatus 10 according to the present embodiment. Explained first will be the structure of an ultrasonic diagnosis apparatus 10 and the flow of signals on the basis of this figure.

The ultrasonic diagnosis apparatus 10 includes an ultrasonic probe 12 which serves to transmit/receive an ultrasonic signal to/from a subject, a device body 11 for driving the ultrasonic probe and processing a received signal from the ultrasonic probe, an input part 13 connected to the device body and capable of inputting instruction information from an operator to the device body, and an ECG 15 for measuring an electrocardiogram waveform. The input part 13 includes a button, a keyboard, and a trackball capable of controlling the diagnosis apparatus and setting various image quality conditions.

The device body 11 comprises an ultrasonic transmitter unit 21, an ultrasonic receiver unit 22, a B-mode processing circuit 23, a Doppler processing circuit 24, an image processing circuit 25, an image memory circuit 26, a display part 28, a heartbeat detection unit 29, a storage medium 30, a controller 31, a network circuit 32, and a graphic circuit 33.

Although not shown, the ultrasonic transmitter unit 21 is comprised of a trigger generator, a delay circuit, and a pulsar circuit, and generates a converged ultrasonic pulse. An echo signal scattered by organs in the subject is received again by the probe 12.

The echo signal outputted for every element is taken in by the ultrasonic receiver unit 22. Although not shown, the echo signal is amplified by a preamplifier for every channel, is supplied with a delay time required for determining a reception directivity, and is added by an adder. A reflection component from the direction corresponding to the reception directivity is emphasized by the addition. A total ultrasonic beam for transmission/reception is formed by the transmission directivity and the reception directivity.

The output from the ultrasonic receiver unit 22 is sent to the B-mode processing circuit 23. Echo signal logarithmic amplification, envelope detection processing, and the like are carried out and converted into data in which signal strength is expressed by the brightness of luminance. The Doppler processing circuit 24 analyzes speed information from the echo signal and sends an analysis result to the image processing circuit 25.

In the image processing circuit 25, a scan line signal sequence is converted into a scan line signal sequence of a general video format represented by TV. The sequence is synthesized with text information or gauges of various setting parameters or graphic images of the present invention, which will be described later, and is outputted as a video signal to the display part 28. Thus, a fault image expressing a subject organ shape is displayed. The display part 28 also functions as a console window to execute various analysis programs.

The image processing circuit 25 executes graphic conversion of time-based change of luminance with respect to an interested area, on the basis of an inputted image signal. The graph is called a TIC (Time Intensity Curve) and is used for quantitatively grasping the process of strengthening an echo signal in the interested area.

The image memory circuit 26 is constructed by a storage memory for storing image data. An operator can read out the information from this memory after diagnosis, so that a motion picture can be reproduced with use of a plurality of images.

A storage medium 30 saves constantly image data in an image memory circuit and also stores various software programs used for an analysis program. For example, the storage medium 30 stores a control program concerning ultrasonic transmission/reception in case of moving a focus point to a specific area specified on an ultrasonic image, which will be described in the second embodiment. Also, the data of the storage medium 30 can be transferred to an external peripheral device through a network circuit 31 by a wired or wireless transfer device.

The graphic circuit 33 is a characterizing part of the present invention and performs image processing again to a diagnosis image generated by the image processing circuit 25, to generate a new image. Or, the graphic circuit 33 generates an image for supporting diagnosis and transfers it to the image processing circuit 25. At this time, the image processing circuit 25 displays an image generated by the graphic processing circuit 33 and a present diagnosis motion image, superimposed by various image processor described later, on the display part 28.

Organic signal information such as an electrocardiogram obtained by the ECG 14 is converted into a digital signal by the heartbeat detection unit 29 and is synthesized with a diagnosis image by the image processing circuit 25. The synthesis result is then displayed on the display part or recorded into the image memory.

The controller 32 has a function as an information processing device (calculator) and is a controller which controls operation of the circuit as required on the basis of an instruction from the input part 13.

The display part 28 is a display device constructed by a CRT and the like.

Subsequently, operation of the ultrasonic diagnosis apparatus 10 will be explained with reference to FIG. 2 in case of executing a diagnosis protocol concerning quantitative analysis (TIC) using a contrast agent.

Figure 2:
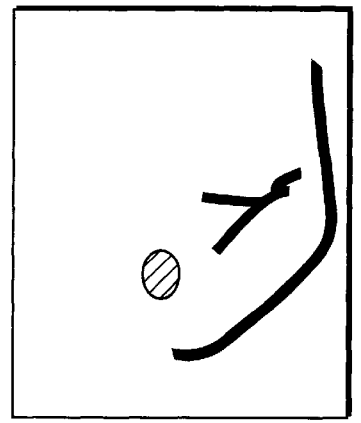
FIG. 2 is a schematic view of an ultrasonic diagnosis image and shows an organ boundary 51, a characterizing portion 52 in an organ, and a main blood vessel 53.

FIG. 2 is a schematic view of an ultrasonic diagnosis image which shows an organ boundary 51 (e.g., an intima of a contour cardiac muscle of a liver or the like), a portion 52 (e.g., a gallbladder in observation of a liver, a valve in a heart, or the like), a main blood vessel 53 (e.g., a main blood vessel in a liver, a carotid artery, or the like), and the like.

In general, an ultrasonic image is recognized such that the organ boundary 51 has higher luminance than organs and the main blood vessel 53 has lower luminance than organs.

As described above, there occurs a necessity to continue observing one same cross-section, when obtaining data used for quantitative analysis. In this case, normally, an operator holds a probe, using features such as the organ boundary 51, the characterizing portion 52 in an organ, or a main blood vessel 53 as marks, thereby to maintain one same cross-section for observation.

The present ultrasonic diagnosis apparatus 10 has a support function in case where the operator needs to maintain one same probe cross-section. That is, when there occurs a necessity to hold one same probe, the operator firstly instructs the controller 21 of the necessity by operating a button or the like through the input part 13. In response to this instruction, the image processing circuit 25 transfers the image data re-constructed at this time point, to the graphic circuit 33. The graphic circuit 33 prepares a "cross-section hold support image", based on the image data, and transfers it to the image processing circuit 25. The image processing circuit 25 synthesizes the cross-section hold support image with a diagnosis image supplied subsequently, and displays them superimposed on the display part 28.

Explanation will now be made of the cross-section hold support image. For example, this image is obtained by supplying an ultrasonic image simply as a reference for holding a cross-section with a transparency and is displayed, superimposed on a diagnosis dynamic image. In this manner, a motion image can be observable through a semi-transparent cross-section hold support image. If the cross-section of the motion image changes, two images are projected, shifted from each other, so that an unnatural image is obtained which the operator can sense.

In addition to the example described above, it is possible to adopt a cross-section hold support image which extracts the contour of an organ or the like. Or, a cross-section hold support image from which the master-servant relationship can be easily grasped can be prepared through relatively easy processing, according to a method which will now be described.

That is, the graphic circuit 33 generates a cross-section hold support image which can be superimposed and displayed in a state which does not hinder observation of a diagnosis motion image, by any of methods (1) to (3) as follows.

(1) With respect to an obtained image, threshold value processing is performed on the luminance level to extract only pixels having luminance equal to or higher than a threshold value and to delete the other pixels. The image of the part extracted by the threshold value processing may be directly used without changes or may be subjected to binary processing and converted into color codes such as read and blue. According to this method, in the example shown in FIG. 2, the organ boundary 51 is mainly extracted.

(2) with respect to an obtained image, threshold value processing is performed on the luminance level, to extract only pixels having luminance equal to or lower than a threshold value and to delete the other pixels. The extracted part is subjected to luminance inversion processing and is converted into color codes after being once added with luminance information. According to this method, the characterizing portion 52 in an organ and mainly the main blood vessel 53 is mainly extracted, in the example shown in FIG. 2.

(3) With respect to luminance level, pixels having luminance higher than a first threshold value and pixels having luminance lower than a second threshold value are extracted and displayed, added with equal luminance information or color information (e.g., a picture like a pen sketch in one color). According to this method, the organ boundary 51, the characterizing portion 52 in an organ, and main blood vessel 53 are mainly extracted in the example shown in FIG. 2.

The structure may be arranged such that only a specific part can be extracted by further performing predetermined processing after extraction of an image according to the methods (1) to (3). This is because if threshold value processing is carried out only on the luminance level, there is a possibility that a bright or dark part of a general speckle pattern (grid stripes) in an organ is extracted. For example, in the method (1), if parts of an organ and the like area imaged, scattered like dots, in addition to the organ boundary 51, information which is not useful as a reference for holding a surface of a fault can be deleted by performing processing, e.g., by limiting the image only to a part having a constant area. As a result, it is possible to extract only an apparently characterizing structure.

Figure 3:
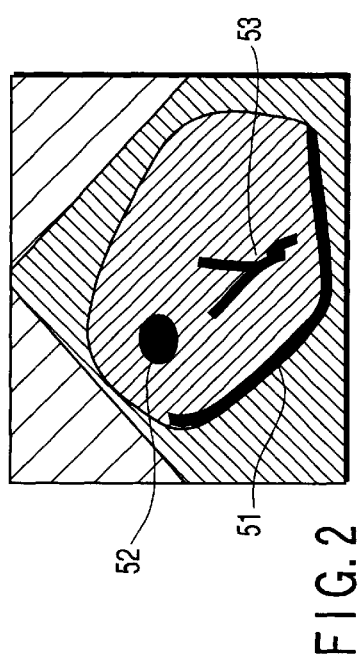
FIG. 3 schematically shows a cross-section hold support image.

FIG. 3 is an image obtained by the method (3) and schematically shows an image in which a characterizing part of an ultrasonic image as a reference for holding a cross-section is marked with a pen or the like. By superimposing this kind of cross-section hold support image on a motion image, the operator can hold a probe while paying attention such that a diagnosis image corresponds to the mark during observation.

The image processing and the superimposing method which have been explained in the present embodiment can be executed with respect to a plurality of images. For example, it is predictable that the heart moves cyclically.

Figure 4:
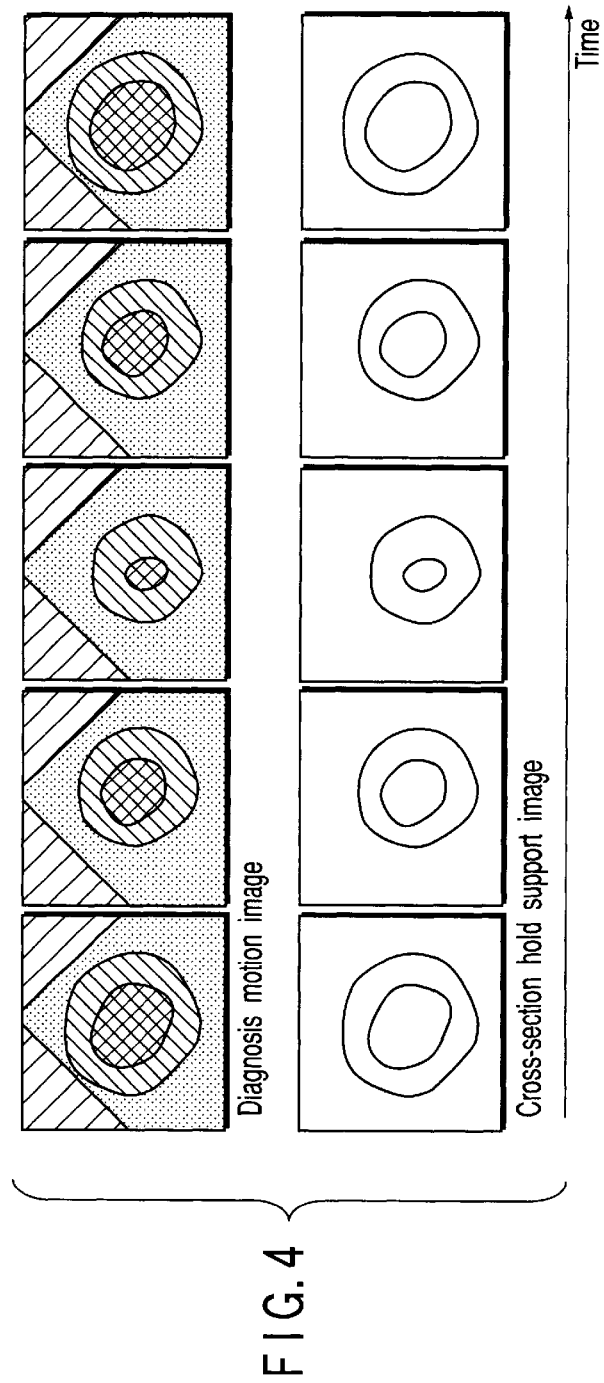
FIG. 4 is a view showing an ultrasonic image of one heartbeat of the heart in an upper stage and a cross-section hold support image at one same heartbeat time phase in a lower stage, such that the upper and lower stages correspond to each other.

FIG. 4 is a view showing an ultrasonic image of one heartbeat of a heart in an upper stage and a cross-section hold support image in the same time-phase of the heart, in a lower stage such that the upper and lower stages correspond to each other.

In this case, a plurality of images equivalent to a cycle of heartbeats are recorded so that the same image processing as described above is carried out by the image processing circuit 25, and the cross-section hold support image in the lower stage shown in FIG. 4 is displayed, superimposed on the corresponding ultrasonic image in the upper stage.

According to this structure, for example, in case where an intima or exine of heart is taken as a characterizing pattern, observation can be carried out so that a drawing equivalent to the intima or exine expands/contracts. Note that this image is added with information concerning the time-based phase of the heartbeat and is displayed and superimposed in synchronization with the time-based phase of heartbeat of the present diagnosis image.

By this support function to obtain securely data necessary for diagnosis/analysis protocol, it is possible to obtain an image in which a characterizing part on an image being inspected is marked with a pen or the like. By using this image as a fault hold support image, an operator can easily execute inspection in which one same fault surface is held if a probe is operated such that a diagnosis image being observed corresponds to the characterizing part of the fault hold support image. As a result, precision of quantitative analysis can be improved.

Second Embodiment

The structure of the ultrasonic diagnosis apparatus according to the second embodiment is the same as that of the ultrasonic diagnosis apparatus 10.

The second embodiment is an example in which diagnosis operation is supported by setting optimal analysis conditions with respect to a desired local area of an ultrasonic image in quantitative analysis using a contrast agent.

In general, it is desired that a signal should be obtained on optimal conditions with respect to all areas, in order to perform analysis on a diagnosis image. However, it is actually known that several parameters as follows vary locally, receiving physical influences.

(1) The transmission sound pressure is the highest near a focus point and decreases more as it is more distant from the focus point.

(2) After passing the focus point, the sound pressure become lower due to influences from organic attenuation as it is deeper after passing the focus point.

Figure 5:
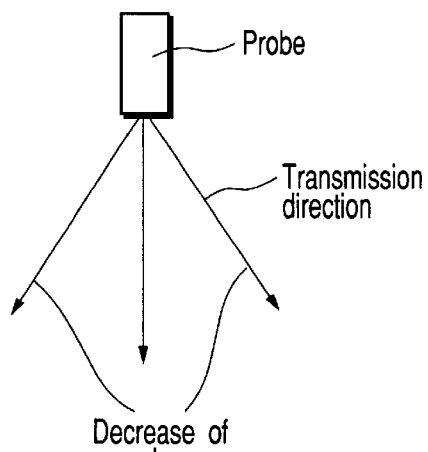
FIG. 5 is a view for explaining a state of distribution of a transmission sound pressure to an end part by electronic scanning.

(3) As shown in FIG. 5, in electronic scanning, the transmission sound pressure at an end part is lower than the transmission sound pressure at a center part because the deflection angle increases.

Figure 6:
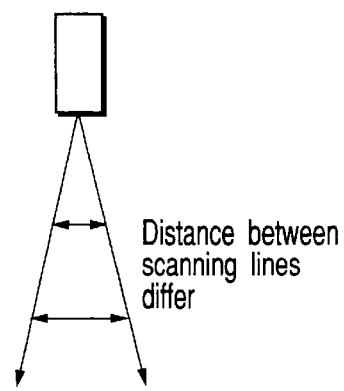
FIG. 6 is a view for explaining the distance between scanning lines in sector scanning.

(4) As shown in FIG. 6, the distance between adjacent scanning lines is gradually widened, particularly in sector scanning.

With respect to these phenomena, problems can be relatively reduced by using a method of generating a relatively uniform sound field, for example, described in Japanese Patent Application No. 2000-150396. However, it is essentially impossible to generate a sound field which is strictly uniform. In addition, if it is tried to attain a uniform sound pressure over the sound field, the transmission power is averaged so that high quality obtained by the strong focus.

In the ultrasonic diagnosis apparatus 10 according to the present embodiment, the following ultrasonic transmission/reception conditions different from the prior art are set with respect to a specified area for the purpose of widening the degree of freedom of an obtained image.

(1) The transmission focus point is set to a specified area.

(2) The ultrasonic transmission drive sound pressure value is reset such that this value is substantially constant at any specified area. Specifically, a correction value is prepared on the basis of a preceding sound field pattern.

(3) The distance between scanning lines is reset such that the distance is substantially constant in a specified area. Specifically, where the angle between adjacent scanning lines is θ, the distance w between scanning lines is expressed by the following.

$$W = x * \sin \theta$$

Therefore, θ may be adjusted at each depth x such that x is constant.

The conditions (1) to (3) are called "optimal analysis conditions".

The area where the optimal analysis conditions are set is instructed through the input part 13 by an operator. As a specific example of operation made by the operator, a cursor displayed on the display part 28 is moved by operating the input part 13 (which is a pointing device capable of indicating a part on a diagnosis image, e.g., trackball, or the like), and a desired area on an ultrasonic image is decided by pushing a button.

Figure 8:
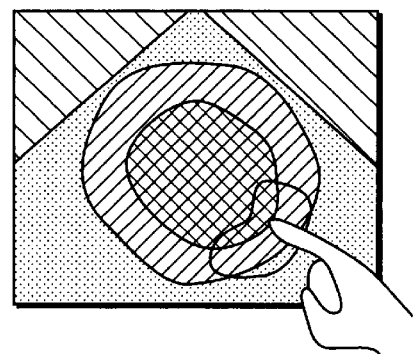
FIG. 8 is a view showing a state in which an operator instructs an interested area by a position detection device provided on the screen of a display part 28.

Also, as shown in FIG. 8, the operator may directly indicates a part on the screen with use of a position detection device provided on the screen of the display part 28, thereby to detect the coordinates of the part.

Figure 7:
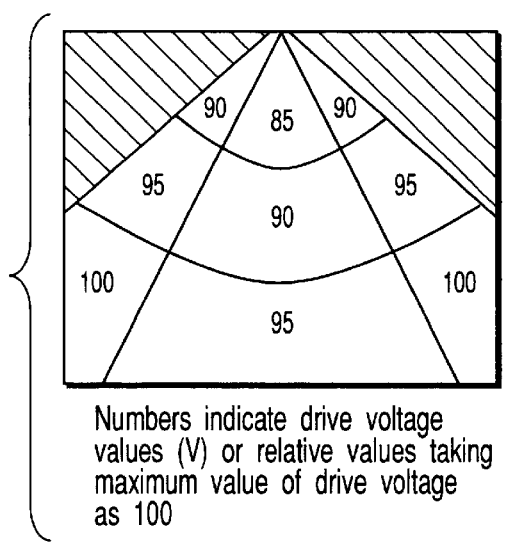
FIG. 7 shows a distribution pattern of an ultrasonic transmission drive sound pressure value concerning a normal ultrasonic image.

Voice of the operator may be identified and an area on an image may be detected, by a microphone provided at the input part 13 and by a voice recognition program included in the controller 32. For example, there can be a structure that the operator says a word of "upper, center, end, lower, deep, right, or left" to move an activated portion among nine divided areas shown in FIG. 7.

When position information thus indicated by the operator is sent to the controller 32, the controller 32 reads transmission/reception condition parameters which comply with the "optimal analysis conditions" from the storage medium 30, thereby to instruct a setting change to each of the circuits in the apparatus body.

Also, the graphic circuit 33 generates a marker for notifying the operator of a point or area on the screen, which is specified by the operator, and displays the marker on the screen. In this case, it is advantageous for diagnosis analysis if an area permitted as an "optimal analysis condition" is specified by the marker.

Meanwhile, as described above, the area specified by the operator is an important part for diagnosis in many cases. Therefore, the specified area may be displayed and enlarged on the display part 28 or may be expressed by scanning lines having a higher density, compared with other unselected areas.

If the above-described method is executed, an excellent image can be obtained in an area where an optimal analysis condition is set, but the image quality may be deteriorated in another area compared with a conventional method. However, the present method realizes a method of optimizing a specified area to widen the degree of freedom in obtaining an image even if other parts are sacrificed. Therefore, if the method is executed, it is preferable to include a device for notifying the operator that photographing which is being presently executed is changed in compliance with "optimal analysis conditions". Specifically, clear indication of an optimal area based on a marker corresponds to the conditions, and there can be a structure in which inside and outside of a marker area are displayed, distinguished from each other, or a structure in which the operator is notified that the present mode is being executed by indicating a text or icon on the screen.

According to a support function to obtain securely data required for a diagnosis/analysis protocol, transmission/reception conditions optimal for quantitative analysis are set with respect to a local interested area specified by an operator. Therefore, the operator can easily prepare conditions which enable quantitative analysis with respect to an interested area during inspection. Also, the above-described operation can be instantly carried out on another area, so that images suitable for quantitative analysis can be obtained in various areas, i.e., in the entire area even in a transient contrast echo.

Third Embodiment

The third embodiment shows an example in which diagnosis/measurement operation is supported by displaying an ultrasonic image in a predetermined form in case where time-based change of a recorded image is analyzed.

In general, there are several attempts to make diagnosis by analyzing time-based change of a recorded image. A representative one of the attempts is a contrast echo of applying a contrast agent. In particular, about one minute immediately after application of a contrast agent is called an early phase, and diagnosis can be made about a benign or malignant tumor and about a portion of ischemia, form the speed or luminance of a contrast agent flowing into each portion of a diagnosis surface and the flow pattern thereof. Further, it is expected that more specific information concerning the extent of progress of a pathological change can be obtained by quantifying them as numerical values.

As has been described in the first embodiment, it is necessary to make observation, holding one same cross-section, when quantitative analysis is carried out. Normally, the most important time in the early phase is 10 to 20 seconds immediately after flow-in of a contrast agent, in many cases. In these cases, the operator instructs a subject to stop breath so that dislocation of a cross-section is reduced.

Figure 9:
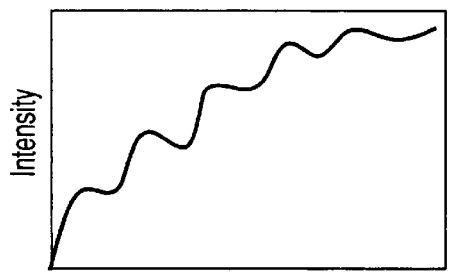
FIG. 9 shows time-based change (TIC) of a luminance histogram measured by a conventional ultrasonic diagnosis apparatus.

However, in these cases, it is essential to receive influences from heartbeats repeated for every about one second. If the time-based change (TIC) of the luminance histogram at one same place is measured, the TIC has cyclical extreme values as shown in FIG. 9, in many cases. This is because there are influences from both of factors that the organ itself moves due to heartbeats and that ejection of blood is synchronized with contraction/expansion of the heart.

In addition, in many cases, averaging processing or the like between measurement values is performed to obtain a smooth curve from the viewpoint of analysis processing, to reduce variants of measurement values of the quantitative analysis. In these cases, however, if the original image itself has many fluctuations, they apparently become a factor which increases an error.

Hence, according to the present embodiment, a group of plural images for every heartbeat are displayed, disposed in one same heartbeat phase, in case of performing quantitative analysis. Also, the quantitative analysis is performed in synchronization with a constant heartbeat time phase.

Figure 10:
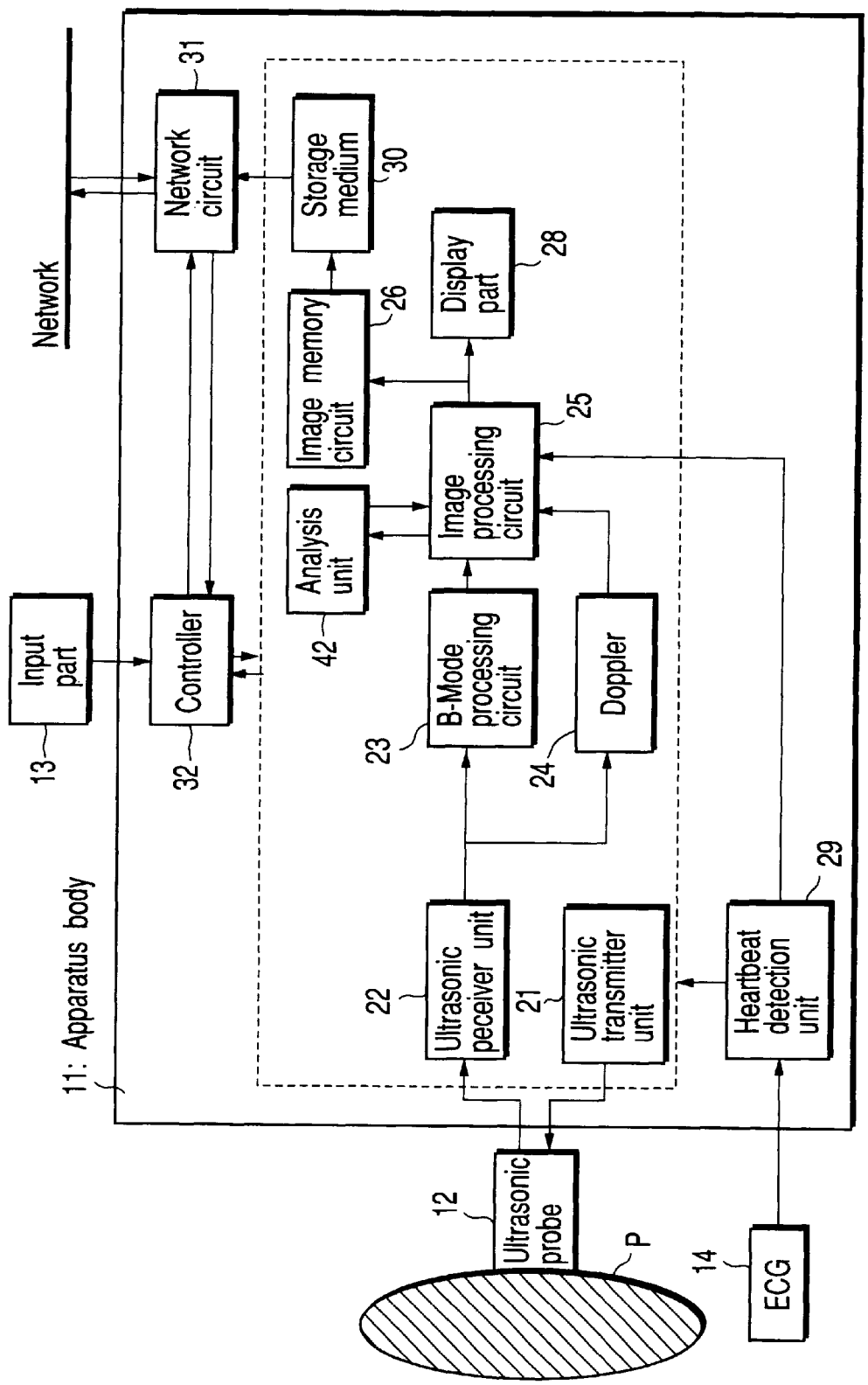
FIG. 10 is a block diagram showing the schematic structure of an ultrasonic diagnosis apparatus 70 according to the third embodiment.

In the following, operation of an ultrasonic diagnosis apparatus according to the third embodiment will be explained with reference to FIG. 10.

The analysis unit 42 is comprised of a software program controlled by a controller 32, and a storage medium. The analysis unit 42 is supplied with an electrocardiogram signal from a heartbeat detection unit 29, and image information of an image memory circuit 26 or at least address information corresponding to an image.

Figure 11:
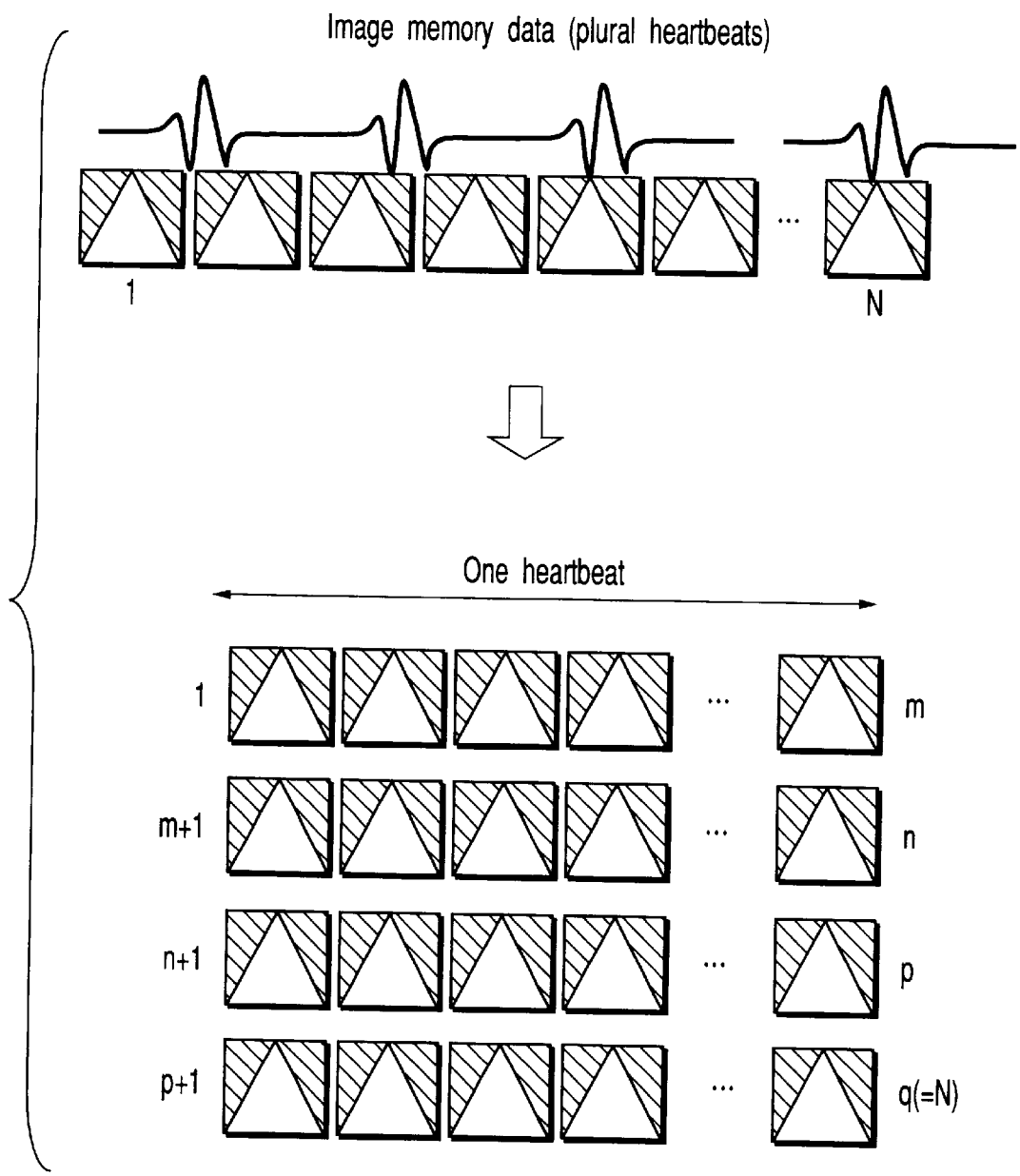
FIG. 11 shows a view in which image data recorded in one-dimensional array in accordance with time is re-arranged into tow-dimensional array information for every heartbeat from electrocardiogram information.

As shown in FIG. 11, the analysis unit 42 rearranges image data recorded in a one-dimensional array based on time, into two-dimensional information, for every heartbeat from the electrocardiogram information. As a result of this, the first direction (the lateral direction in FIG. 11) of the two-dimensional array expresses the time-based change in one cycle of the heartbeat, and the second direction (the longitudinal direction in FIG. 11) expresses the time-based change in the same heartbeat time phase.

Various analysis programs are incorporated in the analysis unit 42. If a program for analyzing the time-based change of a diagnosis image among the programs, the operator can select a group of images with respect to first and second arbitrary directions. For example, as shown in FIG. 12, an image sequence in the second direction can be selected so that a time-based change (TIC) of a luminance histogram based on ultrasonic images of the sequence.

Figure 12:
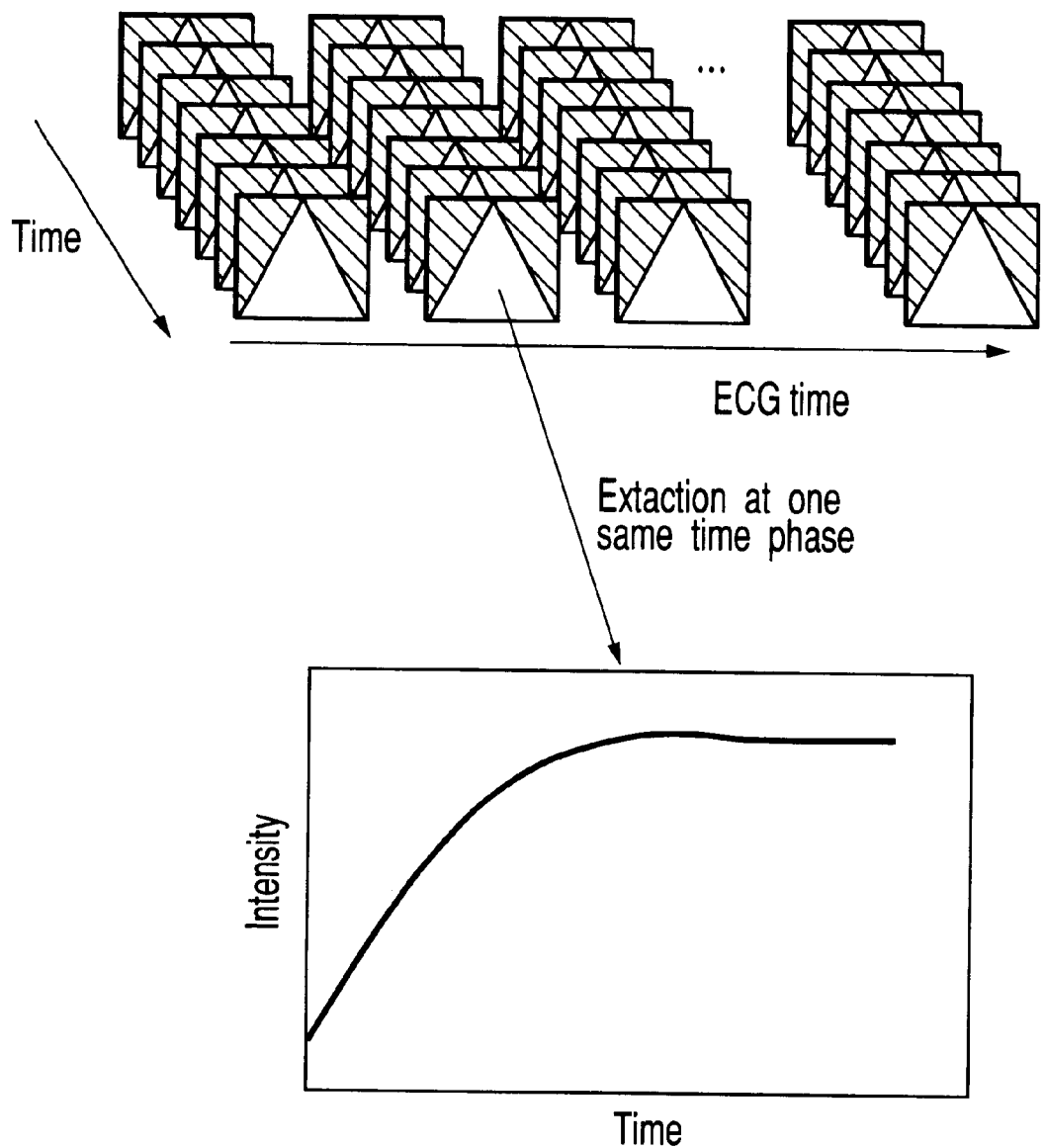
FIG. 12 shows time-based change (TIC) of a luminance histogram measured by an ultrasonic diagnosis apparatus according to the present invention.

Note that the time-based change (TIC) shown in FIG. 12 does not include cyclical extreme values shown in FIG. 9 because this is the TIC which is obtained from an image at one same heartbeat time phase by the support function according to the present embodiment.

The time phase to be analyzed can be arbitrarily set by the operator. A plurality of luminance change curves can be calculated with respect to all time phases. Further, the apparatus comprises calculation programs for obtaining an averaged curve and for making calculations such as addition and subtraction between arbitrary curves, with respect to the plurality of curves, and an interface thereof.

According to this support function for securely obtaining data necessary for a diagnosis/analysis protocol, an image at one same time phase can be extracted in the quantitative analysis, and the organ as a measurement target can be measured at the same time phase. As a result, more stable measurement results can be obtained.

The present invention is not limited to the embodiments described above but may be variously modified without deviating from the scope of the invention in practice. The embodiments may be practiced, properly combined with each other. In this case, combined advantages can be obtained. Further, the embodiments described above include inventions of various stages, and the various inventions can be extracted by a proper combination of a plurality of disclosed components. For example, if the problem described in the column of objects of invention can be solved and at least one of the advantages described in the column of advantages of the invention can be obtained even when several components are deleted from all components, the structure in which the several components are deleted can be extracted as one invention.

As has been explained above, according to the present invention, it is possible to realize an ultrasonic diagnosis apparatus comprising a support function to reduce factors causing analysis errors as much as possible when a diagnosis protocol aiming measurement is executed, and an analysis method using the function.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnosis apparatus which scans inside of a subject with an ultrasonic wave to obtain a cross-sectional image, comprising:

an image generator configured to generate a reference image in which a portion as a reference for holding an equal cross-section is extracted from the cross-sectional image; and a display device configured to display the reference image as a still image, superimposed on a motion image.

2. The apparatus according to claim 1, wherein said image generator extracts the portion as the reference, by threshold value processing.

3. An ultrasonic diagnosis apparatus comprising:

an ultrasonic probe configured to transmit an ultrasonic wave to a subject and receive the ultrasonic wave from the subject;

a generator configured to generate ultrasonic images based on the signal received by said ultrasonic probe;

a memory configured to store a reference image which is an ultrasonic image to adjust a scan position; and a display device configured to display the ultrasonic images generated by said generator as a real-time motion image, superimposed the reference image.

4. The apparatus according to claim 3, wherein the reference image is semi-transparency image.

5. An ultrasonic diagnosis apparatus which scans inside of a subject applied with a contrast agent, with an ultrasonic wave, to obtain a cross-sectional image, comprising:

a display device configured to display an ultrasonic image;

a specification device configured to allow an operator to specify an area of an ultrasonic diagnosis image displayed; and a transmitting unit configured to transmit an ultrasonic wave such that a focus point of transmitting ultrasonic wave is varied to exist in the area specified by said specification device.

6. The apparatus according to claim 5, further comprising: a receiving unit configured to receive an ultrasonic wave such that a focus point of receiving ultrasonic wave is varied to exist in the area specified by said specification device.

7. The apparatus according to claim 5 or 6, wherein said specification device has a pointing device or voice input device configured to specify any of sub areas of the ultrasonic diagnosis image displayed by said display device.

8. The apparatus according to claim 5 or 6, wherein said specification device specifies the sub area, based on contact with the ultrasonic diagnosis image displayed by said display device.

9. The apparatus according to claim 5 or 6, wherein said display device displays information from which it is possible to determine which of the sub areas is the specified sub area.

10. The apparatus according to claim 5 or 6, wherein the sub area is specified at an arbitrary timing.

11. An ultrasonic diagnosis apparatus comprising:

a memory configured to store a plurality of diagnosis image groups in each of which a plurality of diagnosis images collected at a predetermined cycle based on an organic signal of a subject are arranged based on time; and a display device configured to display simultaneously the plurality of diagnosis image groups such that time phases in the predetermined cycle correspond between the groups.

12. The apparatus according to claim 10, wherein the display device displays the plurality of diagnosis images in a two-dimensional matrix defined by a direction in which the diagnosis images are arranged in accordance with time and a direction in which the time phases correspond between groups.

13. The apparatus according to claim 11 or 12, wherein the organic signal is an ECG signal, and the time phase is a heartbeat time phase.

14. The apparatus according to claim 13, further comprising an analyzer configured to perform quantitative analysis based on a plurality of images at one same heartbeat time phase, displayed on said display device.

15. The apparatus according to claim 14, wherein the analyzer performs measurement of a time-based change curve of a luminance histogram.

16. An ultrasonic diagnosis apparatus comprising:

an ultrasonic probe configured to transmit an ultrasonic wave to a subject and receive the ultrasonic wave from the subject;

a receiving unit configured to obtain electrocardiogram signal;

a generator configured to generate an ultrasonic image based on the signal received by said ultrasonic probe; and an analyzer configured to analyze a luminance change curve based on the ultrasonic image obtained when the electrocardiogram signal is at one same heartbeat phase.

17. The apparatus according to claim 16, wherein said analyzer has a function to perform at least one of luminance average calculation, luminance maximum-value calculation, and luminance minimum-value calculation.

18. The apparatus according to claim 16, further comprising a display device configured to display a plurality of analysis curves which are obtained on the basis of a plurality of images at a plurality of same heartbeat time phases and superimposed on a cross-sectional image.

19. The apparatus according to claim 16, further comprising a display device configured to display a plurality of analysis curves at different time phases, superimposed on cross-sectional image.

20. An ultrasonic diagnosis apparatus configured to scan inside of a subject with an ultrasonic wave to obtain a cross-sectional image, comprising:

an image generator configured to generate a plurality of reference images in each of which a portion as a reference for holding an equal cross-section is extracted from the cross-sectional image at a predetermined timing based on an organic signal of the subject; and a display device configured to display a motion image and the reference images synchronized with each other, based on the organic signal of the subject, in superimposed display of the motion image and the reference images.

21. The apparatus according to claim 20, wherein said image generator extracts the portion as the reference, by threshold value processing.

* * * * *